United States Patent [19]

Murphy et al.

[11] Patent Number: 5,672,784
[45] Date of Patent: Sep. 30, 1997

[54] SYNTHESIS OF TETRAFLUOROETHYLENE

[75] Inventors: Patrick Michael Murphy, Parkersburg, W. Va.; Henry Max Schleinitz, Kennett Square, Pa.; David John Van Bramer, Belpre, Ohio

[73] Assignee: E. I. Du Pont de Nemours and Company, Wilmington, Del.

[21] Appl. No.: 643,687

[22] Filed: May 6, 1996

Related U.S. Application Data

[63] Continuation-in-part of Ser. No. 390,017, Feb. 17, 1995, abandoned.

[51] Int. Cl.[6] .................................................. C07C 17/04

[52] U.S. Cl. ................................................................ 570/159
[58] Field of Search ................................................ 570/159

[56] References Cited

FOREIGN PATENT DOCUMENTS 723699  12/1965  Canada ................................. 570/159

*Primary Examiner*—Alan Siegel

[57] ABSTRACT

In the process of pyrolyzing chlorodifluoromethane to form tetrafluoroethylene, yield is improved by having a controlled concentration of perfluorocyclobutane in the feed to pyrolysis.

6 Claims, No Drawings

SYNTHESIS OF TETRAFLUOROETHYLENE

RELATED APPLICATION

This application is a Continuation-In-Part of U.S. Pat. application Ser. No. 08/390,017 filed Feb. 17, 1995 by the same inventor, now abandoned.

FIELD OF THE INVENTION

This invention is in the field of processes for synthesizing tetrafluoroethylene.

BACKGROUND OF THE INVENTION

Tetrafluoroethylene (TFE) is widely used as a monomer in the manufacture of plastic and elastomeric fluoropolymers. The general process for synthesizing TFE by pyrolysis of chlorodifluoromethane ($CF_2HCl$, HCFC-22) is well known in the art, as illustrated by Downing et al. in U.S. Pat. No. 2,551,573. In the idealized reaction, pyrolysis of two moles of $CF_2HCl$ would yield one mole of TFE and two moles of HCl, representing 100% yield to TFE based on carbon and fluorine. In practice, the yield to TFE from converted $CF_2HCl$ is less than 100% because various by-products are formed, some desirable, some not so desirable. One desirable by-product, for example, is hexafluoropropylene (HFP) which is also used as a monomer in fluoropolymers. Other by-products include perfluorocyclobutane ($C_4F_8$) which is considered to be a useful product in the sense that it can be pyrolyzed to give TFE and HFP in good yield. However, it is disadvantageous to do so if TFE and HFP can be synthesized directly.

The effects of pressure and conversion on the yield to TFE from $CF_2HCl$ pyrolysis are discussed, for example, by Scherer, et al. in U.S. Pat. No. 2,994,723, by Halliwell in U.S. Pat. No. 3,306,940, and by Edwards, et al. in U.S. Pat. No. 3,308,174. Generally, yield loss to by-products such as $C_4F_8$ increases with $CF_2HCl$ conversion and with $CF_2HCl$ partial pressure. Halliwell suggests that partial pressure of $CF_2HCl$ is the major factor, rather than total pressure, and hence that the effect of reduced pressure may be achieved by dilution with an inert gas such as nitrogen or helium or carbon dioxide, and shows reduced $C_4F_8$ formation at reduced partial pressure of $CF_2HCl$. Scherer, et al. and Edwards, et al. use steam as diluent in different proportions in pyrolysis of $CF_2HCl$ in order to increase conversion without increasing yield loss to $C_4F_8$ and other high-boiling by-products. Thus, the art offers a wide range of practical conditions for pyrolysis of $CF_2HCl$ to TFE with modest yield loss to by-products such as $C_4F_8$, from low conversion of undiluted feed at atmospheric or higher pressure, to high conversion of diluted feed at low $CF_2HCl$ partial pressure.

Halliwell in U.S. Pat. No. 3,306,940 discloses a process for the co-synthesis of HFP and TFE by pyrolysis of $CF_2HCl$ at conversion in the range 86–94%. As noted by Halliwell, when $CF_2HCl$ is pyrolyzed at low conversion to obtain high yield of TFE, only a small amount of HFP is formed but about two parts of perfluorocyclobutane are formed for each part of HFP. Halliwell further discloses that $C_4F_8$ formed in the pyrolysis reaction can be recycled to the $CF_2HCl$ feed stream for pyrolysis to HFP and TFE with very little yield loss on account of side reactions. Examples 18–21 show 15–45 wt % $C_4F_8$ in $CF_2HCl$ feed to pyrolysis at about 90% $CF_2HCl$ conversion, with 78–100% conversion of the $C_4F_8$. I.e., there is substantial consumption of $C_4F_8$ in these examples of Halliwell's process.

Ukihashi & Hisasue in U.S. Pat. No. 3,459,818 disclose a process for concurrently producing TFE and HFP in which $CF_2HCl$ is partially pyrolyzed, HCl is removed from the pyrolysis product to form a gas mixture consisting essentially of TFE and $CF_2HCl$, and said mixture is then pyrolyzed in a second pyrolysis step. In Examples 1–7, both HFP and $C_4F_8$ were formed in the first partial pyrolysis step, remained in the gas mixture consisting essentially of TFE and $CF_2HCl$, and were present in increased concentration in the product of the second pyrolysis step. Excluding HCl but including $CF_2HCl$, the concentration of $C_4F_8$ was 0.5–2.1 mol % in the gas mixture formed by the first partial pyrolysis and 1.8–6.3 mol % in the product of the second pyrolysis, with $C_4F_8$ concentration always increasing in the second pyrolysis step. Total conversions of $CF_2HCl$ in the examples of Ukihashi & Hisasue are high, in the range 71–97%.

Reduced formation of by-products in the pyrolysis of $CF_2HCl$ in a process aimed at TFE production is desired in order to increase the yield to TFE.

SUMMARY OF THE INVENTION

This invention provides a process comprising pyrolyzing $CF_2HCl$ to obtain tetrafluoroethylene (TFE) as desired reaction product and $C_4F_8$ as undesired reaction product, and further comprising co-feeding $C_4F_8$ along with said $CF_2HCl$ to the pyrolysis reaction in an amount effective to reduce the formation of $C_4F_8$ as said undesired reaction product, essentially without consuming $C_4F_8$ in the pyrolysis reaction, thereby increasing the yield of said TFE reaction product.

DETAILED DESCRIPTION OF THE INVENTION

It has been discovered that addition of $C_4F_8$ to the feed stream for pyrolysis of $CF_2HCl$ to TFE reduces the amount of $C_4F_8$ formed and increases yield to TFE. By adjusting and controlling the concentration of $C_4F_8$ feed, formation of $C_4F_8$ can be essentially eliminated.

As mentioned above, pyrolysis of essentially pure $CF_2HCl$ to form TFE in high yield can result in formation of by-product $C_4F_8$. If one adds $C_4F_8$ in increasing proportions, starting at very low levels, to the $CF_2HCl$ feed stream under the same process conditons, the following effects occur. At low $C_4F_8$ feed levels, the amount of $C_4F_8$ formed is reduced slightly. The amount of $C_4F_8$ formed is the difference between the amount of $C_4F_8$ in the product stream and the amount of $C_4F_8$ in the feed stream. Thus, while the amount of $C_4F_8$ in the product stream will be greater than for the case with no $C_4F_8$ in the feed stream, the difference between the amounts in product and feed streams will be smaller. As the amount of $C_4F_8$ in the feed stream is increased from low levels, the amount of $C_4F_8$ formed is further reduced. The amount of $C_4F_8$ in the feed stream can be further increased, with further accompanying reduction in the amount of $C_4F_8$ formed, until the amount of $C_4F_8$ in the product stream is about equal to the amount of $C_4F_8$ in the feed stream. Under this condition, the amount of $C_4F_8$ formed is essentially zero, and the formation of $C_4F_8$ in the pyrolysis reaction may be said to have been eliminated. This general behavior is illustrated by the examples below. If $C_4F_8$ concentration in the feed stream is increased beyond that required to eliminate $C_4F_8$ formation, then the amount of $C_4F_8$ in the product stream will be less than the amount in the feed stream. That is, $C_4F_8$ will be consumed in the pyrolysis reaction. The process of this invention is intended to operate without consuming $C_4F_8$. As one skilled in the art will recognize, the condition for zero formation of $C_4F_8$ may not be sharply defined, because the rate of change of $C_4F_8$ formed with concentration of $C_4F_8$ in the feed stream may be low at feed concentrations near the value for exactly zero $C_4F_8$ formation.

The process of this invention is intended to synthesize TFE at high yield, such as 88% or more, from converted $CF_2HCl$. Any process conditions that result in high yield can be used. One generally desires to operate at conversion as high as possible consistent with high yield. As discussed above, yield losses and, therefore, yield depend on conversion and partial pressure of $CF_2HCl$. For example, conversions of 90% and higher can be employed to obtain high yield at low $CF_2HCl$ partial pressure of the order of 0.05 atm, as illustrated by Edwards, et al. for pyrolysis under steam dilution conditions. Vanishingly small partial pressures of $CF_2HCl$ have the obvious drawback of requiring larger equipment for given output. On the other hand, pyrolysis of undiluted $CF_2HCl$ at 4 atm pressure and 23% conversion may not deliver high yield, as illustrated by Downing's Example II. To achieve high yield in pyrolysis of undiluted $CF_2HCl$ at near-atmospheric pressure, conversion is typically in the range 10–50%, preferably 25–45%. To achieve high yield in pyrolysis of diluted $CF_2HCl$, conversion can be as high as 30–90% depending on degree of dilution ($CF_2HCl$ partial pressure).

As is well known in the art, conversion can be controlled by adjusting temperature and/or residence time in the reactor. There are no particular constraints on temperature and residence time, except that the combination of residence time and the temperature of the gas exiting the furnace should be low enough to prevent overconversion of $CF_2HCl$ and to avoid transition into conditions that favor synthesis of higher proportions of HFP along with TFE. Reaction conditions that can be used in the process of this invention are generally the same as conditions employed in the absence of $C_4F_8$ co-feed with $CF_2HCl$ for pyrolysis to TFE. Generally, reaction temperatures in the range 700°–1000° C. as indicated by reactor wall temperature, preferably 750°–850° C. can be used. For processes operating near atmospheric pressure and in the absence of diluent, mass velocities in the range 20–80 kg/m²·s, preferably 25–55 kg/m²·s, and gas exit velocities in the range 20–80 m/s, preferably 30–50 m/s, can be used. Under these conditions, flow is turbulent but not super-sonic. The choice of conditions, of course, will be influenced if not limited by the design of the reactor to be used. Since productivity is usually a practical concern, combinations of higher mass velocity and higher temperature are usually favored over combinations of lower mass velocity and lower temperature.

As discussed above, diluent substances such as steam (water vapor) or carbon dioxide can be present during the pyrolysis of $CF_2HCl$. The use of diluents, especially steam, is within the scope of this invention. However, excessive dilution with steam, e.g., beyond 95% of total pressure, has the drawback of yield loss to hydrolysis and resultant formation of CO with its attendant separation difficulties. (See Edwards et al.) When steam dilution is employed, steam concentrations in the range of 25–95% of total pressure are ordinarily used.

The process of this invention can be carried out in any reactor equipment suitable for the pyrolysis of $CF_2HCl$ to make TFE. In particular, tube furnaces conventionally used for such pyrolysis can be used. In such furnaces, the tubes are usually made of corrosion-resistant alloy, such as Inconel®600 (The International Nickel Company). Heat for the endothermic reaction of this process can be supplied by any suitable means, such as by external heating, by induction heating, by injection of hot diluent (e.g., steam), by a combination of the foregoing, and the like.

$CF_2HCl$ is the principal reactive component of the feed stream for the process of this invention. Because $CF_2HCl$ and HFP form an azeotrope that has composition of about 0.15 mole of HFP for each mole of $CF_2HCl$, and unconverted $CF_2HCl$ is typically recycled, it is convenient to include HFP in the feed along with $CF_2HCl$. However, the presence of HFP in the feed is believed to have little influence on the reaction and is not required in the practice of this invention. Generally, the amount of HFP in the product stream is slightly greater than that in the feed stream, corresponding to the small amount of HFP formation noted by Halliwell. Other halocarbon compounds, for example, by-products of the process that are desirably recycled such as $C_2F_5Cl$, can be present in small concentration.

The amount of $C_4F_8$ fed along with $CF_2HCl$ depends on the result desired. It may, for example, be desired to form a small amount of $C_4F_8$ but less than the amount that would be formed with no $C_4F_8$ in the feed. In general, formation of $C_4F_8$ increases slightly with increasing conversion of $CF_2HCl$, and the amount of $C_4F_8$ required in the feed to eliminate $C_4F_8$ formation increases accordingly. Roughly, the amount of $C_4F_8$ in the feed required to eliminate $C_4F_8$ formation is 15× the amount formed under the same conditions in the absence of $C_4F_8$ feed. In the process of this invention, there is at least as much $C_4F_8$ in the product stream from reaction as in the feed stream. The difference between the amounts of $C_4F_8$ in the product and feed streams is a measure of $C_4F_8$ formation. As shown by the examples to follow, as little as 1 wt % $C_4F_8$ in the feed, based on combined weight of $CF_2HCl$ and $C_4F_8$, produces a discernible reduction in formation of $C_4F_8$. For high-yield pyrolysis at $CF_2HCl$ partial pressure of about 1 atm, concentrations of 5–10 wt % are preferred. Extrapolation of experimental data obtained under these conditions to zero formed $C_4F_8$ indicates that formation is essentially eliminated at feed concentration in the range 8–10 wt %, which is most preferred. When $C_4F_8$ concentration in the feed exceeds about 10–12 wt %, then, under these operating conditions $C_4F_8$ will be consumed. That is, there will be less $C_4F_8$ in the exit stream than in the feed stream. The process of this invention is intended to reduce or eliminate formation of $C_4F_8$ without consuming $C_4F_8$ in the pyrolysis of $CF_2HCl$. The concentration of $C_4F_8$ in the feed stream that eliminates formation of $C_4F_8$ varies with the reaction conditions. For high-yield pyrolysis of $CF_2HCl$ diluted with steam, the amount of $C_4F_8$ required in the feed to eliminate $C_4F_8$ formation (essentially without consuming $C_4F_8$) varies with the degree of dilution, but can range up to about 18 wt % based on combined weight of $CF_2HCl$ and $C_4F_8$ for high dilution and total pressure near atmospheric pressure. Concentrations of $C_4F_8$ in the range 6–16 wt % are especially effective under these conditions, preferably 8–16 wt %.

As one skilled in the art will recognize, attempts to operate so as to exactly eliminate $C_4F_8$ formation may be handicapped by inexact process control. Thus, operation with this objective may be characterized by variation about the balance point, with periods of reduced $C_4F_8$ formation, periods of exact balance, and periods of $C_4F_8$ consumption averaging over time to give approximately zero $C_4F_8$ formation. That is, formation of $C_4F_8$ is essentially eliminated on a time-average basis. This is considered to be within the scope of the invention.

Any convenient pressure can be used for the process of this invention. Total pressures of about 0.4–1.5 atm are especially convenient. $CF_2HCl$ partial pressures of no more than about atmospheric pressure are preferred.

The feed stream can be cold when introduced into the pyrolysis furnace, or can be preheated. Thus, feed stream temperatures in the range 0°–500° C. can be used. Feed stream temperature in the range 300°–450° C. is preferred.

EXAMPLES

Experiments were carried out using a tube furnace under conditions characterized by temperature, mass velocity, and gas exit velocity given in the individual examples below. Pyrolysis stream flows were turbulent. All experiments were conducted at total pressure slightly in excess of atmospheric presssure. The feed stream was heated to about 350° C. for all examples. Reaction temperature (T) is reported as tube temperature measured by a thermocouple placed on the exterior surface at a position three-fourths of the length of the tube from the inlet end.

The base feed stream for the following examples was principally $CF_2HCl$ and HFP in the molar ratio of about 92/8. The stream also contained small amounts, less than 2 mol %, of other chlorofluorocarbon compounds, principally $C_2F_5Cl$. Perfluorocyclobutane was added to this base stream in different amounts to explore the effect of feed concentration on the amount of $C_4F_8$ generated during pyrolysis. The amount of $C_4F_8$ introduced was determined by an orifice flowmeter and its concentration in the feed stream was measured using a gas chromatograph (GC). The concentration of $C_4F_8$ in the feed stream is given on the basis of $C_4F_8$ and $CF_2HCl$ combined.

Product stream components were separated by distillation.

GC measurements were used to determine the conversion of $CF_2HCl$ and the yields to TFE and HFP based on converted $CF_2HCl$. As is customary in the art, yield calculations were based on the $CF_2$ content of $CF_2HCl$. Yields are presented as the sum of TFE and HFP yield. The yield to HFP, after deducting HFP in the feed, was essentially constant at about 1% throughout the tests reported in the examples. GC could not be used reliably to measure small changes in low concentrations of $C_4F_8$, so a mass balance approach was used. $C_4F_8$ was isolated and accumulated in a weigh tank from which net production was determined. $C_4F_8$ was simultaneously withdrawn from the same tank at the rate required for the feed to the reaction, so that at steady state the rate of $C_4F_8$ accumulation was the rate of net $C_4F_8$ formation (net generation). The net formation of $C_4F_8$ is stated relative to the amount of TFE produced. TFE concentration in the product stream was determined by GC.

EXAMPLE 1

This example summarizes results for tests having $CF_2HCl$ conversion centered at about 37%, mass velocity in the range 29–46 kg/m²·s, and gas exit velocity in the range 37–43 m/s. Other conditions are shown in Table 1. As stated above, $C_4F_8$ feed concentration (wt %) is based on combined weight of $C_4F_8$ and $CF_2HCl$, and $C_4F_8$ formation is based on the amount of TFE formed (wt/100wt TFE). Analytical results also given in Table 1 show that $C_4F_8$ produced decreased and yield to TFE and HFP increased as $C_4F_8$ feed concentration was increased. From these data, it was estimated that $C_4F_8$ feed concentration of about 9.9 wt % would result in zero production of $C_4F_8$.

TABLE 1

| Conditions and Results for Example 1 | | | | |
|---|---|---|---|---|
| T (°C.) | Conversion (% $CF_2HCl$) | $C_4F_8$ Feed (wt %) | $C_4F_8$ Produced (wt/100 wt TFE) | Yield (TFE + HFP, %) |
| 780 | 37.2 | 0.13 | 1.60 | 91.7 |
| 785 | 37.8 | 1.62 | 1.25 | 94.5 |
| 782 | 36.5 | 2.53 | 1.31 | 95.8 |
| 786 | 36.3 | 5.08 | 0.48 | 96.5 |

EXAMPLE 2

This example summarizes results for tests having $CF_2HCl$ conversion centered at about 31%, mass velocity in the range 41–48 kg/m²·s, and gas exit velocity in the range 38–45 m/s. Other conditions are shown in Table 2. Analytical results also given in Table 2 show that $C_4F_8$ produced decreased and yield to TFE and HFP increased as $C_4F_8$ feed concentration was increased, with $C_4F_8$ production decreasing to a very low value at feed concentration of 6.52 wt %. From these data, it was estimated that $C_4F_8$ feed concentration of about 9.3 wt % would result in zero production of $C_4F_8$.

TABLE 2

| Conditions and Results for Example 2 | | | | |
|---|---|---|---|---|
| T (°C.) | Conversion (% $CF_2HCl$) | $C_4F_8$ Feed (wt %) | $C_4F_8$ Produced (wt/100 wt TFE) | Yield (TFE + HFP, %) |
| 785 | 30.7 | 0.24 | 1.89 | 93.2 |
| 779 | 30.3 | 1.69 | 1.61 | 94.0 |
| 773 | 31.4 | 2.92 | 1.20 | 94.6 |
| 774 | 32.4 | 6.52 | 0.27 | 96.1 |

EXAMPLE 3

This example summarizes results for tests having $CF_2HCl$ conversion centered at about 28%, mass velocity in the range 40–44 kg/m²·s, and gas exit velocity in the range 37–41 m/s. Other conditions are shown in Table 3. Analytical results also given in Table 3 show that $C_4F_8$ produced decreased and yield to TFE and HFP increased as $C_4F_8$ feed concentration was increased, with $C_4F_8$ production decreasing to a very low value at feed concentration of 7.65 wt %. From these data, it was estimated that $C_4F_8$ feed concentration of about 9.0 wt % would result in zero production of $C_4F_8$.

TABLE 3

| Conditions and Results for Example 3 | | | | |
|---|---|---|---|---|
| T (°C.) | Conversion (% $CF_2HCl$) | $C_4F_8$ Feed (wt %) | $C_4F_8$ Produced (wt/100 wt TFE) | Yield (TFE + HFP, %) |
| 775 | 29.0 | 0.25 | 1.82 | 94.5 |
| 768 | 27.6 | 5.02 | 0.54 | 95.3 |
| 775 | 28.9 | 6.69 | 0.27 | 95.6 |
| 775 | 28.1 | 7.65 | 0.24 | 95.9 |

We claim:

1. Process comprising pyrolyzing $CF_2HCl$ to obtain tetrafluoroethylene as desired reaction product and $C_4F_8$ as undesired reaction product, and further comprising co-feeding $C_4F_8$ along with said $CF_2HCl$ to the pyrolysis reaction in an amount effective to reduce the formation of $C_4F_8$ as said undesired reaction product, essentially without consuming $C_4F_8$ in the pyrolysis reaction, thereby increasing the yield of said tetrafluoroethylene reaction product, said $CF_2HCl$ and said $C_4F_8$ co-fed with said $CF_2HCl$ being the essential compounds fed to the pyrolysis reaction, said pyrolysis reaction being carried out under a total pressure of 0.8 to 1.2 atmospheres to a conversion of $CF_2HCl$ of from 10% to 50%, the concentration of said $C_4F_8$ being 5% to 10% based on the combined weight of $C_4F_8$ and $CF_2HCl$.

2. The process of claim 1 wherein said $C_4F_8$ concentration is from 8% to 10%.

3. The process of claim 1 wherein said yield of tetrafluoroethylene from converted $CF_2HCl$ is at least 88%.

4. Process comprising pyrolyzing $CF_2HCl$ to obtain tetrafluoroethylene as desired reaction product and $C_4F_8$ as undesired reaction product and further comprising co-feeding $C_4F_8$ along with said $CF_2HCl$ to the pyrolysis reaction in an amount effective to reduce the formation of $C_4F_8$ as undesired reaction product, essentially without consuming $C_4F_8$ in the pyrolysis reaction, thereby increasing the yield of said tetrafluoroethylene reaction product, said $CF_2HCl$ and said $C_4F_8$ co-fed with said $CF_2HCl$ being the essential compounds fed to said pyrolysis reaction, said pyrolysis reaction being carried out in the presence of inert diluent providing 25% to 95% of the total pressure of said pyrolysis reaction, said pyrolysis reaction being carried out at a total pressure of 0.8 to 1.2 atmosphere and conversion of said $CF_2HCl$ of from 30% to 90%, the concentration of said $C_4F_8$ being 6% to 16% based on the combined weight of $C_4F_8$ and $CF_2HCl$.

5. The process of claim 4 wherein said diluent is steam.

6. The process of claim 4 wherein said yield of tetrafluoroethylene from converted CF2HCl is at least 88%.

* * * * *